US007390295B2

(12) United States Patent
Hatami

(10) Patent No.: US 7,390,295 B2
(45) Date of Patent: Jun. 24, 2008

(54) PORTABLE CYCLIC ORIFICE PENETRATING DEVICE

(76) Inventor: James Hatami, 29063 High Sierra Trail, Saugus, CA (US) 91390

( * ) Notice: Subject to any disclaimer, the term of this patent is extended or adjusted under 35 U.S.C. 154(b) by 471 days.

(21) Appl. No.: 11/088,359

(22) Filed: Mar. 24, 2005

(65) Prior Publication Data

US 2005/0215852 A1 Sep. 29, 2005

Related U.S. Application Data

(60) Provisional application No. 60/556,237, filed on Mar. 24, 2004.

(51) Int. Cl.
*A61F 5/00* (2006.01)

(52) U.S. Cl. ........................................................ 600/38

(58) Field of Classification Search ............. 600/38–41; 128/895, 845, 897–899
See application file for complete search history.

(56) References Cited

U.S. PATENT DOCUMENTS

| | | | | |
|---|---|---|---|---|
| 4,790,296 A * | 12/1988 | Segal | | 601/97 |
| 5,851,175 A * | 12/1998 | Nickell | | 600/38 |
| 5,853,362 A | 12/1998 | Jacobs | | |
| 6,142,929 A | 11/2000 | Padgett | | |
| 6,599,236 B1 * | 7/2003 | Castro | | 600/38 |
| 6,902,525 B1 * | 6/2005 | Jewell | | 600/38 |
| 7,056,281 B2 * | 6/2006 | Bookwalter et al. | | 600/38 |
| 2002/0103415 A1 * | 8/2002 | Manska et al. | | 600/38 |

* cited by examiner

*Primary Examiner*—Samuel G Gilbert

(57) ABSTRACT

A cyclic orifice penetrating device according to the present disclosure may include portable frame for supporting the penetration drive mechanism. The frame provides three degrees of adjustment to permit adjustment for a range of user physiques as well as multiple use modes. A drive mechanism according to the present disclosure includes a motor driven, generally conical cam to activate the cam follower. The cams may be formed to have a number of profiles and may be easily removed and replaced to permit the penetration device to simulate a variety of user partners. The cam follower may be laterally adjusted across the cam during use to permit the user to control the amount of cyclic lateral travel of the penetrating element or elements. The motor speed may also be adjusted by the user to suite user preferences.

11 Claims, 10 Drawing Sheets

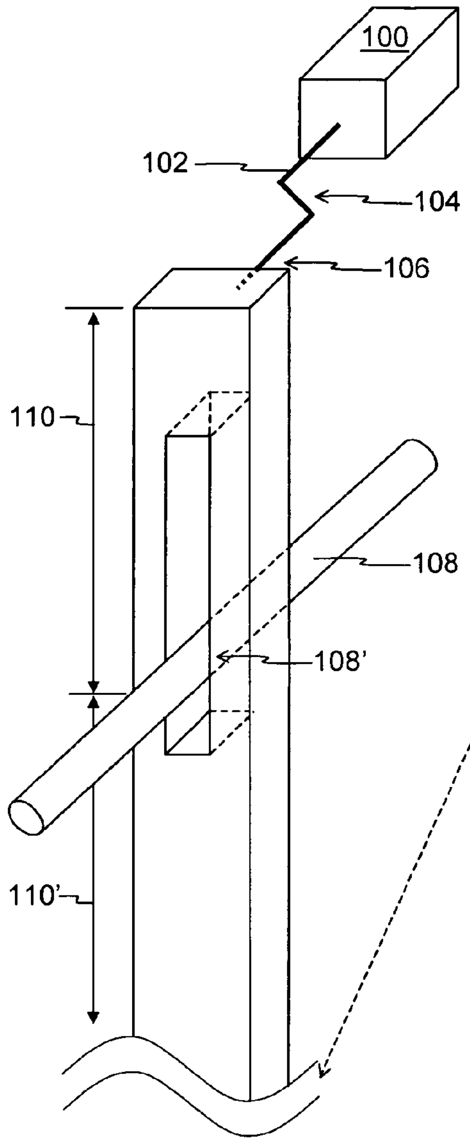
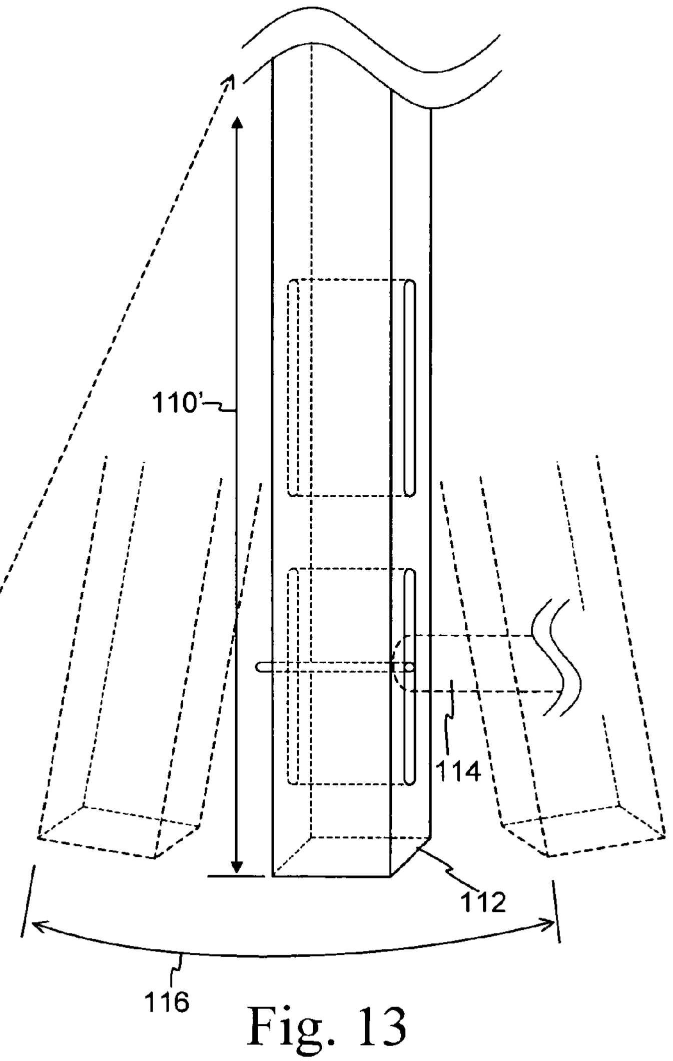
Fig. 13
Fig. 12

PORTABLE CYCLIC ORIFICE PENETRATING DEVICE

This application claims the priority of U.S. provisional application Ser. No. 60/556,237 filed Mar. 24, 2004.

FIELD OF THE INVENTION

This invention relates to orifice penetrating devices and more specifically to a powered, cyclic orifice penetrating devices.

DESCRIPTION OF THE PRIOR ART

Conventional orifice penetrating devices are generally manually actuated and rely on the user or another person for cyclic penetration. Other conventional devices may require the user to adopt an uncomfortable position or orientation. This may detract from the experience.

What is needed is a cyclic penetrating device that is self driving and capable of simulating human interaction and permits the user to adopt generally conventional positions.

SUMMARY OF THE INVENTION

In a first aspect, the present disclosure provides a portable frame for supporting the penetration drive mechanism. The frame provides multiple degrees of adjustment to permit adjustment for a range of user physiques as well as multiple use modes. Three or more leg of the frame may be permanently or removably secured to a mat or pad to provide more stability. The frame may also provide a stable platform for the drive mechanism to simulate human interaction. The frame may also be folded for easy storage and transport.

In another aspect, the present disclosure provides a motor driven, generally conical cam to activate the cam follower. Suitable cams may be formed to have a number of profiles and may be easily removed and replaced to permit the penetration device to simulate a variety of user partners. The cam follower may be laterally adjusted across the cam during use to permit the user to control the amount of cyclic lateral travel of the penetrating element or elements. The motor speed may also be adjusted by the user to suite user preferences.

In another aspect of the present disclosure the cam follower may include multiple attachment points for connecting one or more penetrating elements. Attachment of multiple penetrating elements permits simultaneous penetration of multiple user orifices.

In another aspect of the present disclosure, penetrating elements may include one or more electric heating elements, an electric vibrator, or other suitable electric accessory. Electricity for the penetrating element accessories may be conducted through two or more electric hot points adjacent the attachment point for energizing the penetrating element.

In a still further embodiment of the present disclosure a motor using an offset driveshaft may use lever arm multiplication and an adjustable pivot point to drive a penetrating element and provide an adjustable range of penetration.

These and other features and advantages of this disclosure will become further apparent from the detailed description and accompanying figures that follow. In the figures and description, numerals indicate the various features of the disclosure, like numerals referring to like features throughout both the drawings and the description.

BRIEF DESCRIPTION OF THE DRAWINGS

FIG. 12 is a perspective view of an alternate drive embodiment according to the present disclosure.

FIG. 13 is a perspective view of the engagement end of the alternate embodiment drive of FIG. 12.

DETAILED DESCRIPTION OF THE PREFERRED EMBODIMENT(S)

Figure 1:
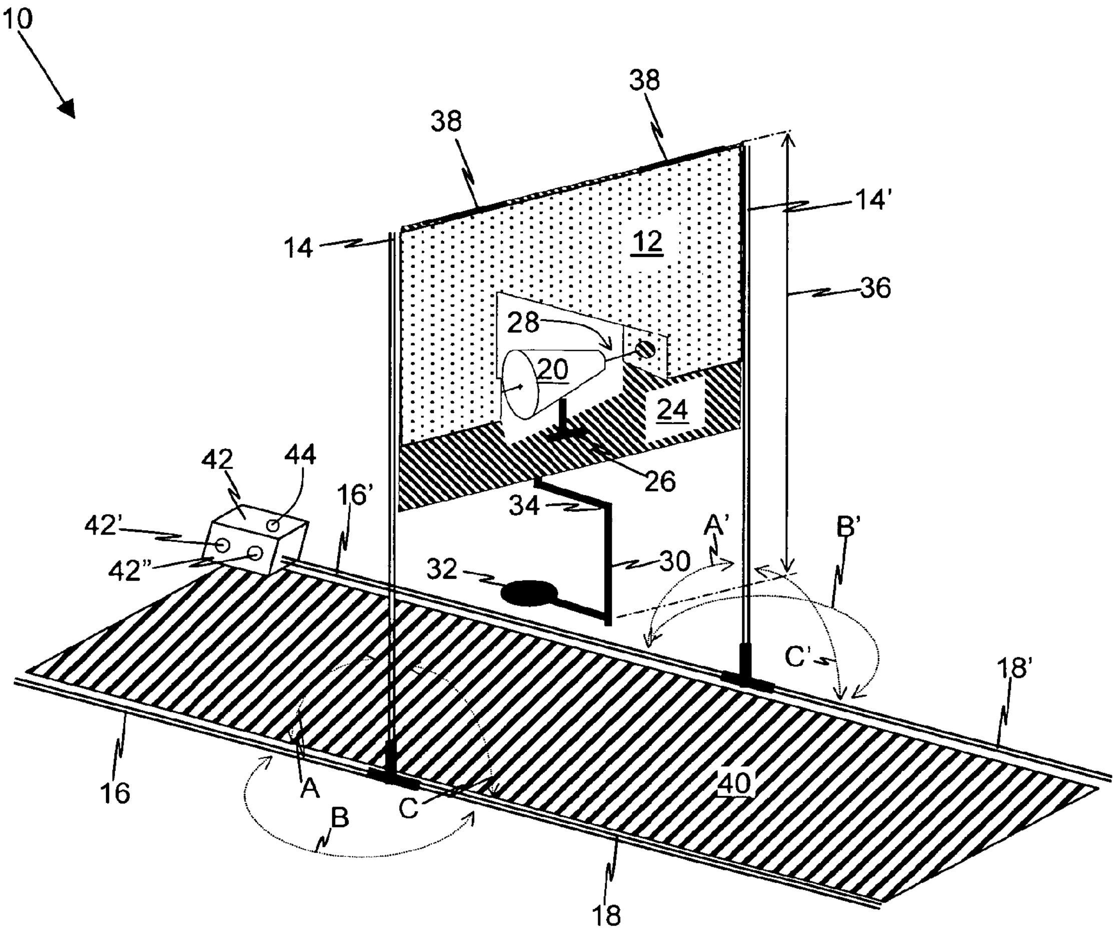
FIG. 1 is a perspective view of a penetrating device according to the present disclosure.

Referring now to FIG. 1, penetrating device 10 includes drive structure 12 secured to support legs 14 and 14'. Support legs 14 and 14' are further supported by stabilizer legs 16 and 18, and stabilizer legs 16' and 18' respectively. Drive structure 12 includes one or more drive cams such as cam 20 powered through axle 28 by motor 22 (on FIG. 2). Movement of cam 20 drives action plate 24. Action plate 24 is connected to drive structure 12 by one or more hinges 38. Moveable cam follower 26 is connected to action plate 24 and imparts cyclic thrust movement to action plate 24 proportional to movement of cam 20. Engagement arm 34 is also connected to action plate 24 and conveys the cyclic thrust movement of action plate 24 to engagement end 30 and to one or more suitable engagement devices such as penetrating element 32 attached thereto.

The length that engagement arm 34 extends from pivot points such as hinges 38, such as length 36, operates as a lever arm multiplier and multiplies the cyclic thrust movement of action plate 24 and imparts the multiplied cyclic thrust movement to the one or more penetrating elements 32.

Stabilizer leg 16 may be adjusted to rotate through arcs A and B relative to support leg 14 and stabilizer leg 18 to fold for storage and to provide variable support geometry and accommodate user preferences. Similarly, stabilizer leg 18 may be adjusted to rotate through arcs C and B relative to support leg 14 and stabilizer leg 16 for storage and to provide variable support geometry and accommodate user preferences. Stabilizer leg 16' may be adjusted to rotate through arcs A' and B' relative to support leg 14' and stabilizer leg 18' for storage and to provide variable support geometry and accommodate user preferences. Similarly, stabilizer leg 18' may be adjusted to rotate through arcs C' and B' relative to support leg 14' and stabilizer leg 16' for storage and to provide variable support geometry and accommodate user preferences.

A mat or pad such as pad 40 may also be an element of penetrating device 10. Pad 40 may extend along legs 16 and 18 and legs 16' and 18'. Pad 40 may permanently or removably engage legs 16, 16', 18 and 18'. Any suitable means of engagement may be used. In a currently preferred embodiment of the present disclosure pad 40 is made of nylon and engages legs 16, 16', 18 and 18' using conventional hook and loop fastener straps.

Figure 4:
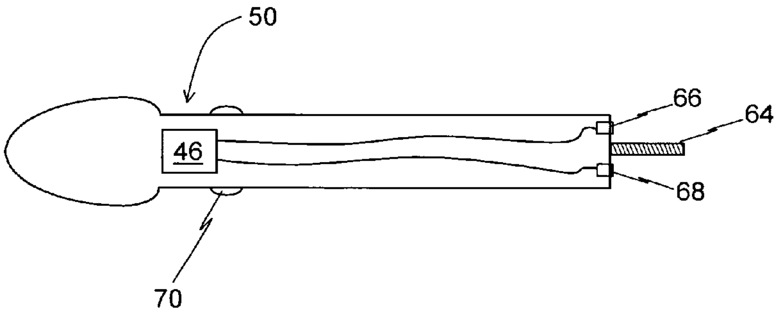
FIG. 4 is a cutaway view of the penetrating element of the device of FIG. 1.

Remote control 42 may be attached to any suitable leg to provide control of motor 22, cam follower 26, and any included electric elements of penetrating element 32. Controls such as control 42' may be used to control the application of power and the speed of motor 22, and control 42" may be used to control the lateral position of cam follower 26, and accessory controls such as accessory control 44 may be used to control the status, on or off and speed, of accessories such as vibrator 46 in penetrating element 50 as shown in FIG. 4. Remote control 42 may be wired directly to penetrating device 10 or it may use any suitable wireless connection such as but not limited to rf and infrared.

Cam 20 may rotate about an axis of rotation such as axle 28. Rotation of cam 20 drives cam follower 26. Cam follower 26 is adjustably attached to action plate 24 and cyclic motion corresponding to the profile of cam 20 may be imparted to action plate 24 through cam follower 26. Engagement arm 34 is removable attached to action plate 24 and thus applies the cyclic motion of action plate 24 to any penetrating elements attached thereto such as penetrating element 32. Engagement end 30 of engagement arm 34 may include one or more penetrating elements such as penetrating element 32.

Figure 2:
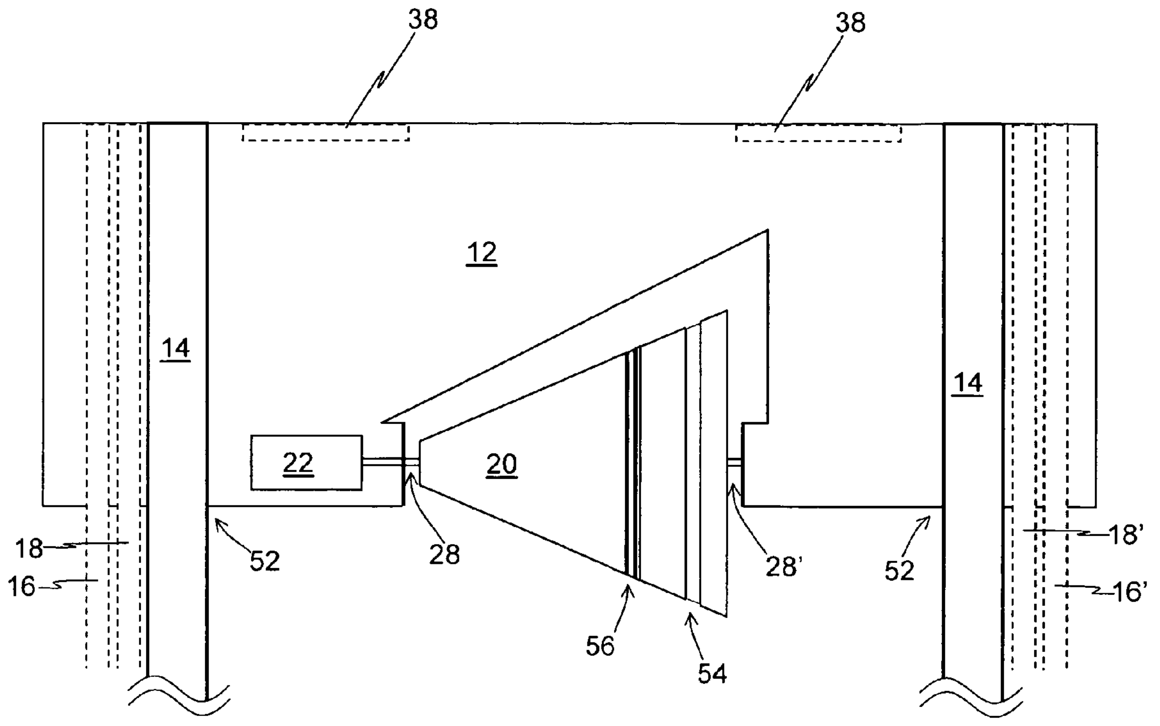
FIG. 2 is a front view of the drive mechanism of the device of FIG. 1.

Referring now to FIG. 2, in storage position 52, legs 14, 16, and 18 may be pivoted to be adjacent each other at drive structure 12 as shown, and legs 14', 16' and 18' may be pivoted to be adjacent each other at drive structure 12 as shown. Cam 20 may have any suitable profile and may include one or more channels or slots such as slot 54. Slot 54 may provide a profile differing from the general profile of cam 20 and may also control lateral movement of cam follower 26 and prevent wandering or unintended lateral movement of cam follower 26 during use of penetrating device 10. In addition to a varying profile and channels or slots, a cam such as cam 20 may also include bumps or ribs such as ribs 56. The width, depth and period of ribs 56 may vary along with the profile of cam 20, or it may be preselected and uniform on a given cam.

To enable a cam to be easily changed, shaft 28' may be spring loaded, and drive shaft 28 may be splined for connection to motor 22.

Figure 3:
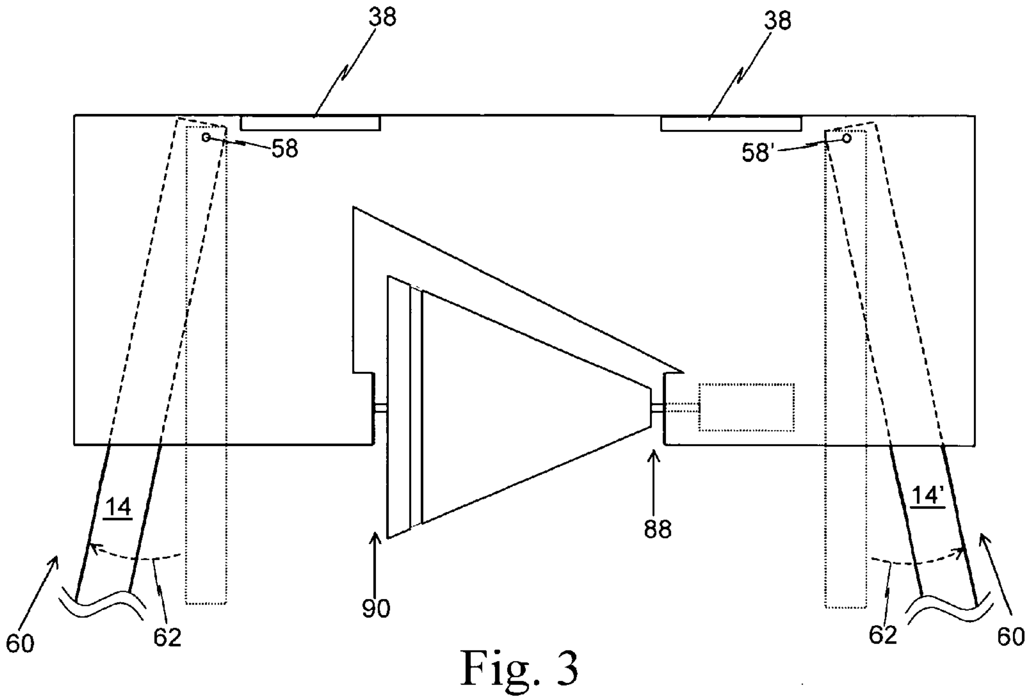
FIG. 3 is a back view of the drive mechanism of the device of FIG. 1.

Referring now to FIG. 3, in a reverse view of FIG. 2, drive structure 12 attaches to legs 14 and 14' at pivot points 58 and 58' respectively. From storage position 52 leg 14 may pivot through arc 62 to use position 60. Similarly, leg 14' may pivot through arc 62 to use position 60. Cam 20 includes driven end 88 and idler end 90.

Referring now to FIG. 4, penetrating element 50 may be attached to engagement end 30 using attachment element 64. Attachment element 64 may be a threaded screw, a quick release element, or any other suitable device. Hot point 66 and 68 may connect with similar points on engagement end 30 to conduct electricity to penetrating element 50. Electricity may power any suitable accessory to penetrating element 50 such as vibrator 46. Penetrating element 50 may have any suitable composition and may also include one or more ribs or other tactile surface elements such as rib 70.

Figure 14:
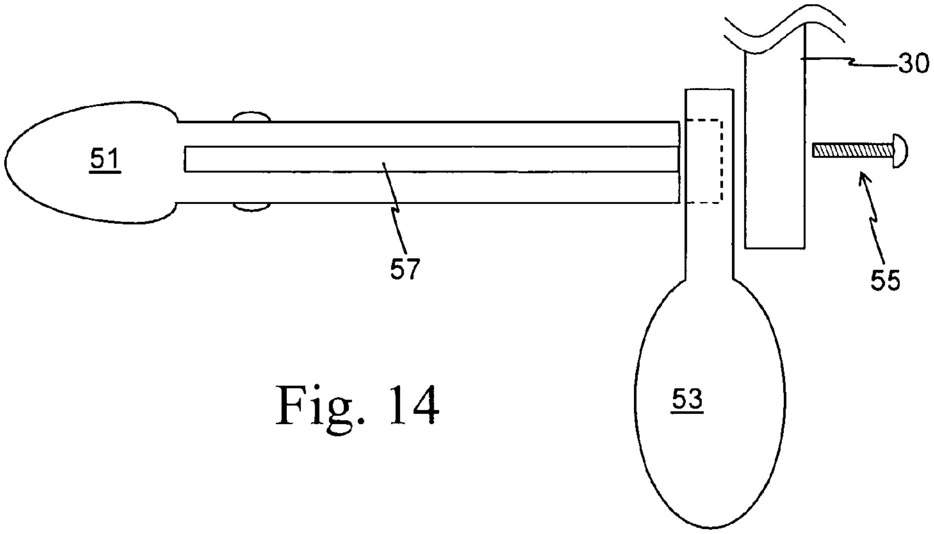
FIG. 14 is a side view of an alternate penetrating element with attachments according to the present disclosure.

In another alternate embodiment of the present disclosure, penetrating element 50 may also include a heating element. Conventional dildos may be attached to engagement end 30 using a screw or other suitable attachment means. Other attachments may also be secured to engagement end 30 such as but not limited to simulated testicles 53 such as shown in FIG. 14.

Figure 5:
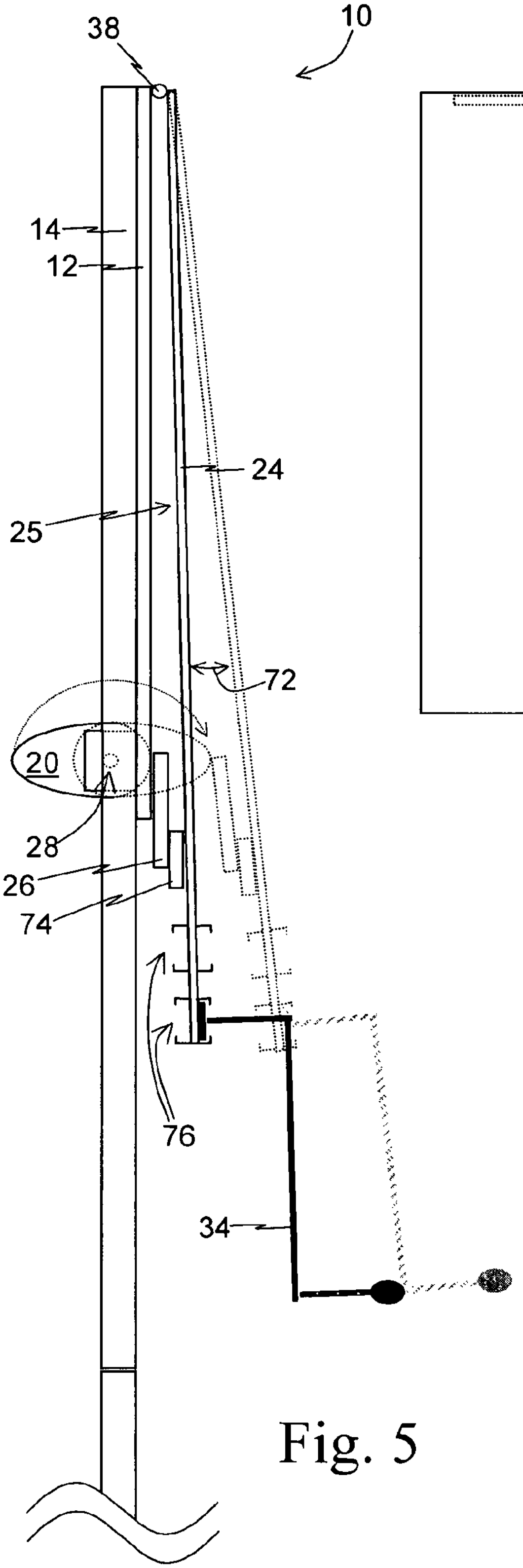
FIG. 5 is a side view of the device of FIG. 1.
Figure 6:
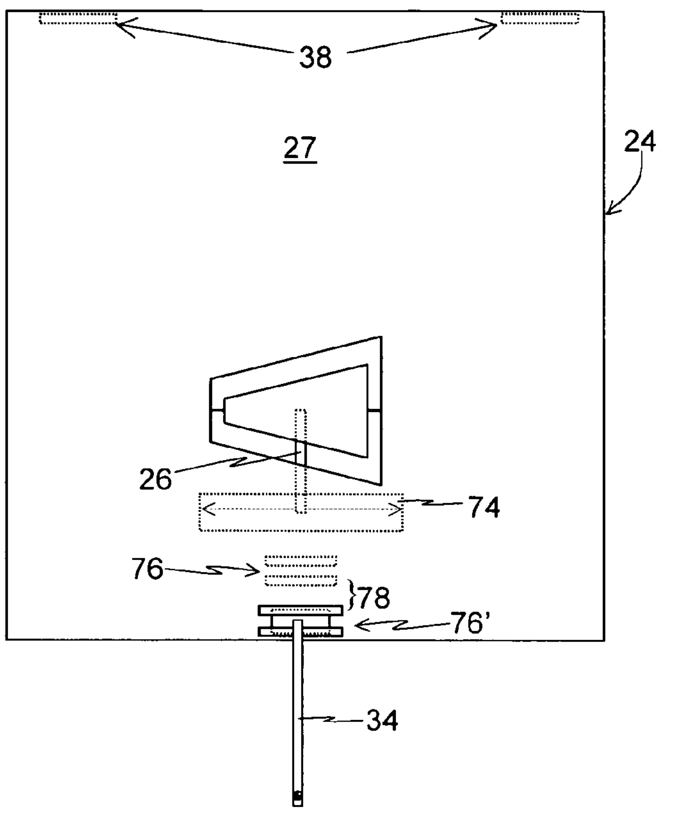
FIG. 6 is a back view of a drive plate according to the present disclosure.

Referring now to FIG. 5 and FIG. 6, in a side view of penetrating device 10, cam 20 is shown as rotating about axle 28 and causing action plate 24 to move through arc 72. In a currently preferred embodiment of the present disclosure hinges 38 may include one or more springs or other biasing elements to retain cam follower 26 in contact with cam 20 as cam 20 rotates. Cam follower 26 is secured to action plate 24 using control apparatus 74. Control apparatus 74 provides control of the lateral position of cam follower 26. The lateral position of cam follower 26 may be altered using remote control 42. Remote control 42 may provide one or more drive signals to control apparatus 74.

Action plate 24 may include one or more sets of attachment brackets such as brackets 76. In a currently preferred embodiment of the present disclosure, two sets of brackets 76 may be secured to action plate 24. First brackets 76 may be offset from second brackets 76' by offset 78. First brackets 76 may also be attached to a first side 25 of action plate 24 and second brackets 76' may be attached to second side 27 of action plate 24. Brackets 76 may be used to secure or otherwise removably attach engagement arm 34.

Figure 7A:
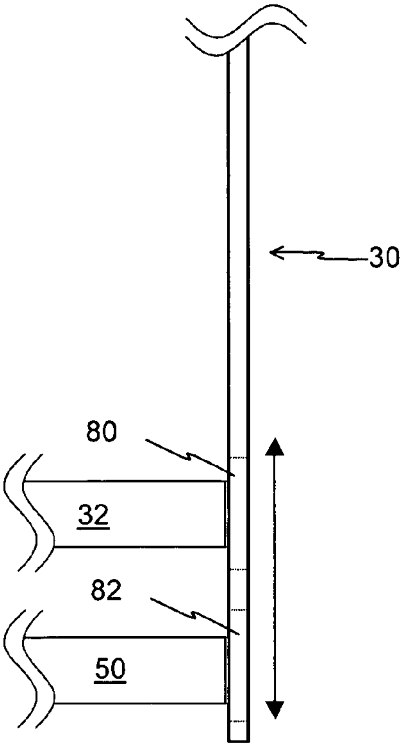
FIG. 7A is a side view of the engagement end of the device of FIG. 1 showing two penetrating elements.
Figure 7B:
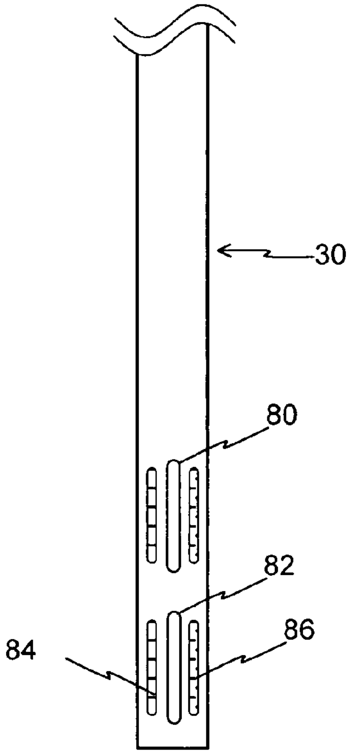
FIG. 7B is a front view of the engagement end of the device of FIG. 1.

Referring now to FIG. 7A and FIG. 7B, engagement end 30 may include one or more penetrating element attachment locations such as attachment location 80 and attachment location 82. For example, penetrating element 32 may be secured at attachment location 80, while penetrating element 50 may be simultaneously secured at attachment location 82. Electrical contacts such as contact 84 and contact 86 may be provided on engagement end 30 to conduct electricity to hot points 66 and 68 of penetrating element 50. The electricity available through contacts 84 and 86 may be controlled by one or more controls on remote control 42.

Figure 8:
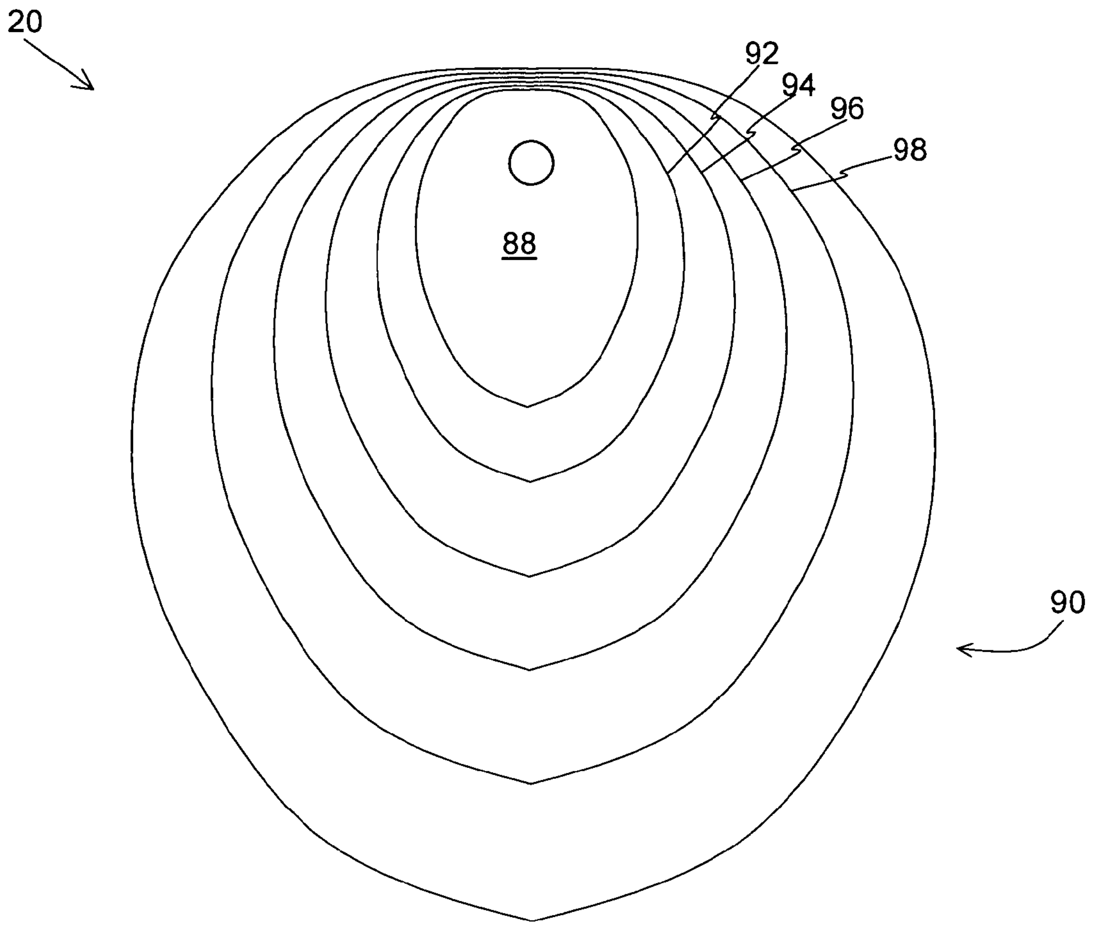
FIG. 8 is an end view of a drive cam according to the present disclosure.
Figure 9:
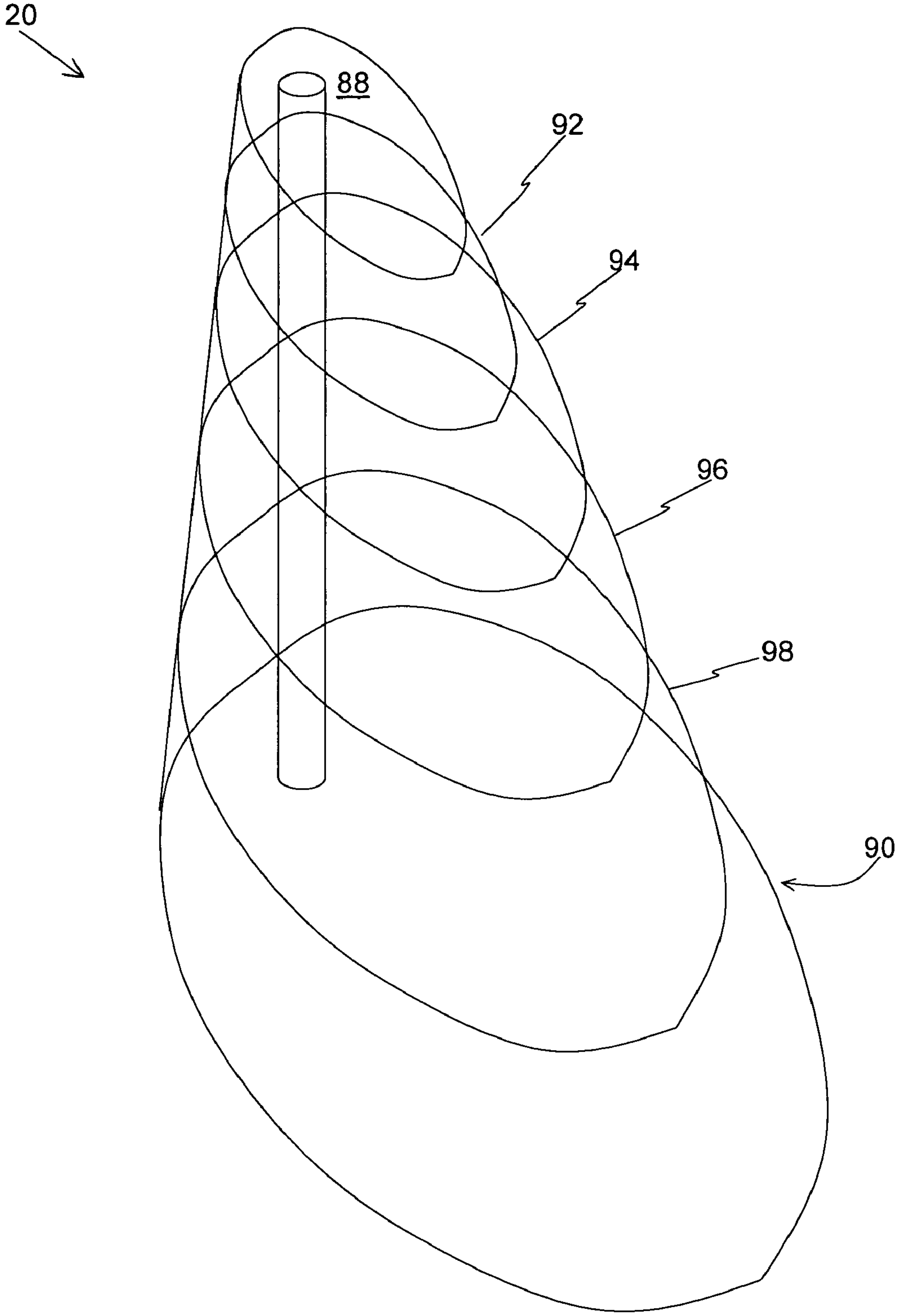
FIG. 9 is a side view of the cam of FIG. 8.

Referring now to FIG. 8 and FIG. 9, cam 20 may have any suitable profile. In a first embodiment, cam 20 includes contours 92, 94, 96 and 98 between driven end 88 and idler end 90.

Figure 10:
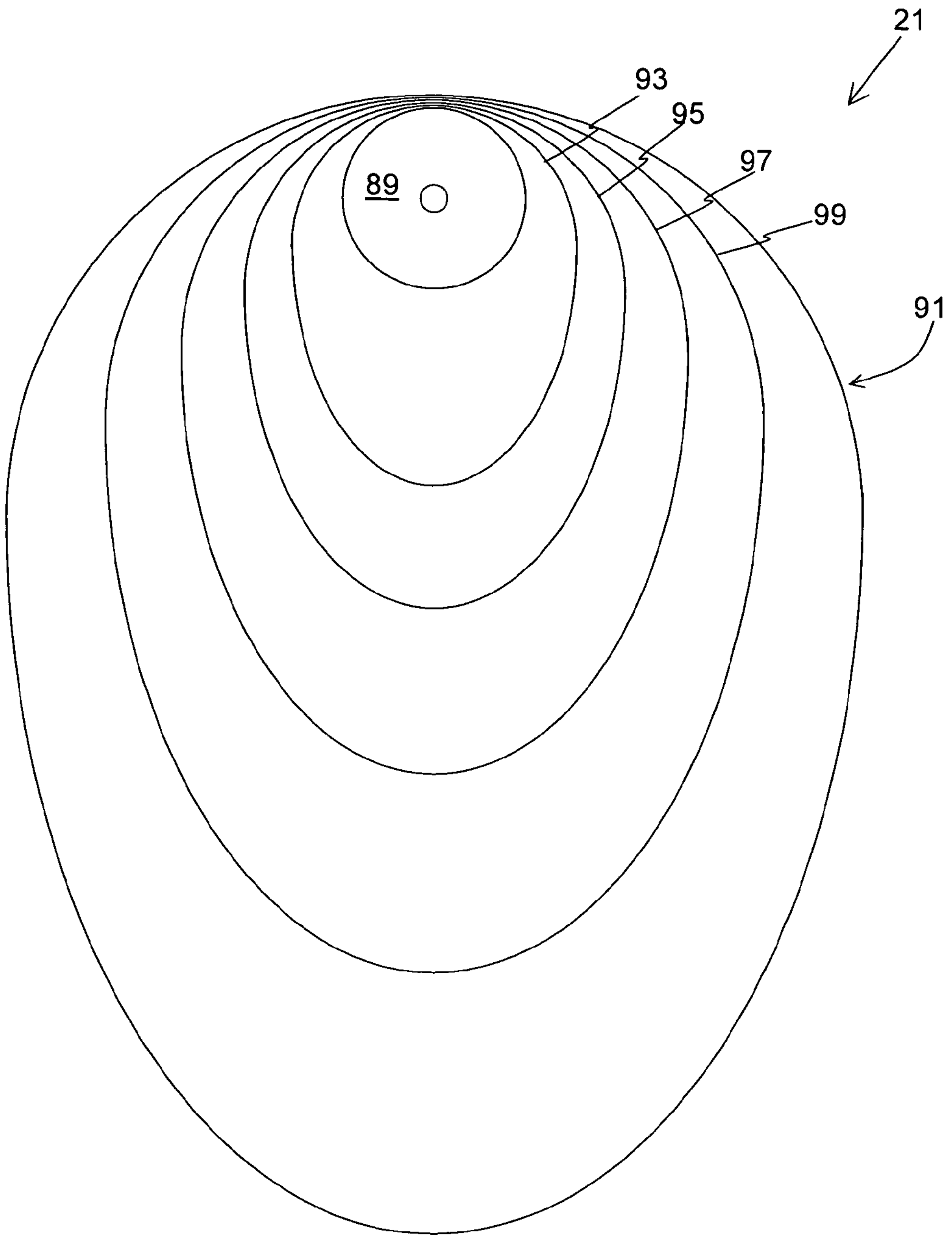
FIG. 10 is an end view of an alternate drive cam according to the present disclosure.
Figure 11:
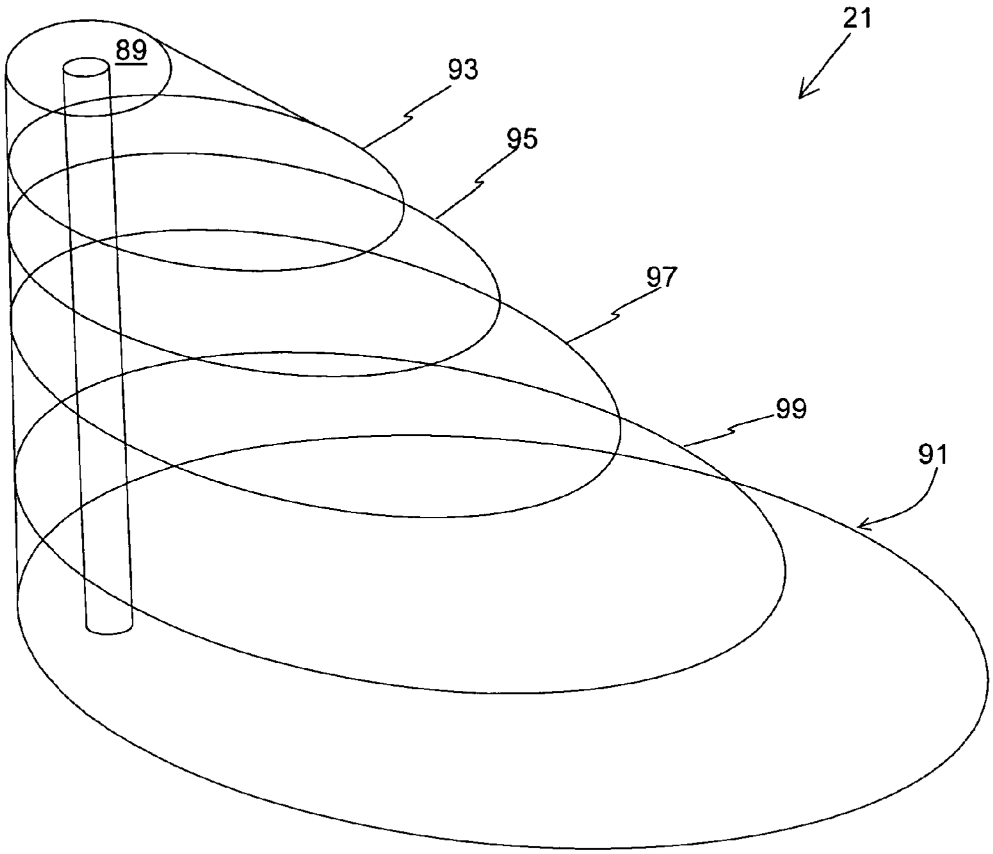
FIG. 11 is a side view of the cam of FIG. 10.

Referring now to FIG. 10 and FIG. 11, cam 21 may have any suitable profile. In an alternate embodiment, cam 21 includes contours 93, 95, 97 and 99 between driven end 89 and idler end 91. While the present disclosure includes two alternate embodiments of cam profiles, they do not represent the full breadth of suitable profiles. Any suitable profile may be used.

Referring now to FIG. 12, motor 100 may rotate driveshaft 102. Driveshaft offset 104 may cause driven end 106 to move cyclically relative to moveable pivot 108. The relationship between driven lever length 110 and penetrator lever length 110' multiplies the cyclic motion of driven end 106 to drive penetrating end 112 and the one or more penetrating elements such as penetrating element 114. Changing position 108' of moveable pivot 108 enables adjustment of range of penetration 116.

Referring now to FIG. 14, in an alternate configuration of the present disclosure penetrating element 51 may be a conventional dildo or other suitable penetrating element and may be connected to engagement end 30 using any suitable attachment element such as screw 55. Attachments such as attachment 53 may also be connected to engagement end 30 to provide additional stimulation for the user. Penetrating element 51 may also include one or more components suitable for stimulating human orifices. For example penetrating element 51 may include one or more stiffening elements such as stiffening element 57 or penetrating element 51 may have two different composition materials to provide predictable resilience and stiffness.

Having now described the invention in accordance with the requirements of the patent statutes, those skilled in the art will understand how to make changes and modifications in the present invention to meet their specific requirements or conditions. Such changes and modifications may be made without departing from the scope and spirit of the invention as set forth in the following claims.

I claim:

1. An apparatus for cyclic orifice penetration comprising:
- a support frame;
- a motor secured to the support frame;
- one or more cams rotated by the motor;
- a cam follower engaging the one or more cams;
- an engagement arm secured to the cam follower on an action plate, the engagement arm also having a engagement end; and
- one or more penetrating elements secured to the engagement arm at the engagement end.

2. The apparatus of claim 1 wherein the support frame is foldable.

3. The apparatus of claim 1 wherein the penetrating elements are shaped like a human penis.

4. The apparatus of claim 1 wherein the penetrating element includes a controllable heater.

5. The apparatus of claim 1 wherein the penetrating element includes one or more vibrating elements.

6. The apparatus of claim 1 further comprising: a remote control for controlling one or more controllable parameters of the apparatus.

7. The apparatus of claim 6 wherein the one or more controllable parameters of the apparatus are selected from the list:
- motor power;
- motor speed;
- cam follower position;
- accessory heater power;
- accessory vibrator power.

8. The apparatus of claim 6 wherein the remote control is wireless.

9. The apparatus of claim 6 wherein the one or more cams further comprises;
- one or more slots on a cam, the one or more slots aligned perpendicular to the axis or rotation of the one or more cams.

10. The apparatus of claim 1 wherein the penetrating element includes one or more stiffening elements.

11. An apparatus for cyclic orifice penetration comprising:
- a support frame;
- a motor secured to the support frame;
- one or more cams rotated by the motor, said one or more cams having one or more slots on a cam, the one or more slots aligned perpendicular to the axis or rotation of the one or more cams, wherein one or more of the one or more slots further includes one or more ribs parallel to the axis of rotation of the one or more cams;
- a cam follower engaging the one or more cams;
- an engagement arm secured to the cam follower on an action plate, the engagement arm also having a engagement end;
- one or more penetrating elements secured to the engagement arm at the engagement end; and
- said apparatus having a remote control for controlling one or more controllable parameters of the apparatus.

* * * * *